United States Patent [19]
Shih

[11] Patent Number: 6,061,176
[45] Date of Patent: May 9, 2000

[54] MICROSCOPE SYSTEM FOR OBSERVATION AND DISPLAY OF MICROCIRCULATION AT MULTIPLE BODY AREAS

[76] Inventor: Song Hsin Shih, No.3-2, Alley 5, Lane 217, Sec. 3, Chung Shiao E. Rd., Taipei, Taiwan

[21] Appl. No.: 09/152,126

[22] Filed: Sep. 14, 1998

[51] Int. Cl.[7] .................................................. G02B 21/00
[52] U.S. Cl. ........................ 359/368; 359/385; 600/310
[58] Field of Search ..................................... 359/363, 385, 359/389, 368; 351/206, 213, 221; 600/310, 476

[56] References Cited

U.S. PATENT DOCUMENTS

| | | | |
|---|---|---|---|
| 4,311,358 | 1/1982 | Gibbons | 359/385 |
| 4,498,749 | 2/1985 | Hoover | 354/79 |
| 4,680,635 | 7/1987 | Khurana | 358/211 |
| 5,612,263 | 3/1997 | Filmer | 501/71 |
| 5,734,498 | 3/1998 | Krasieva | 359/387 |
| 5,891,730 | 4/1999 | Li | 436/8 |
| 5,904,994 | 5/1999 | Dodabalapur | 428/690 |
| 5,983,120 | 11/1999 | Groner | 600/310 |

OTHER PUBLICATIONS

Dictionary of Scientific and Technical Terms, McGraw–Hill, Feb. 1978.

Primary Examiner—Cassandra Spyrou
Assistant Examiner—Leo Boutsikaris
Attorney, Agent, or Firm—Bacon & Thomas

[57] ABSTRACT

Disclosed is a microscope system for observation and display of microcirculation of blood at multiple body areas. The system includes an optical microscope and a display system. The optical microscope includes an electronic flash light and a scotopic detector to take instantaneous photos of images of microcirculation of blood of an observed object. An analog-to-digital conversion circuit converts video simulated signal into digital image signals that can be processed by a computer and are stored in an image memory. In an image card, the image signals in the image memory are stacked to digital graph signals stored in a graph memory, the resultant signals are converted into video simulated signals by a digital-analog conversion circuit and are output to a monitor, so that images of microcirculation of blood are displayed on the monitor.

1 Claim, 5 Drawing Sheets

WINDOW NO. 1 :    THE PARAMATER OF FIRST VESSEL
AREA: (u m²) 1050

DIAMETER: (um) 10.5
                                    VELOCITY(mm/s)
.4  .5  .52  .5  .5  .55  .6  .65  .65  .65  .65  .65
.65  .62  .65  .65  .65  .6  .55  .5  .5  .45
AVERAGE AREA(u m²) 1050    DIAMETER: (um) 10.5  VELOCITY(mm/s)

Measuring the blood velocity and cross-sectional diameter of arteries.

WINDOW NO. 1 :    THE PARAMATER OF SECOND VESSEL
AREA: (u m²) 1650

DIAMETER: (um) 16.5

-.16  -.26  -.26  -.31  -.31  -.31  -.26  -.21  -.23  -.26  -.33
-.41  -.43  -.43  -.38  -.33  -.28  -.23  -.18  -.16  -.16  -.11

Graph of blood velocity in arterioles and venules
AVERAGE AREA(u m²) 1650    DIAMETER: (um) 16.5  VELOCITY(mm/s)

Measuring the blood velocity and cross-sectional diameter of veins.

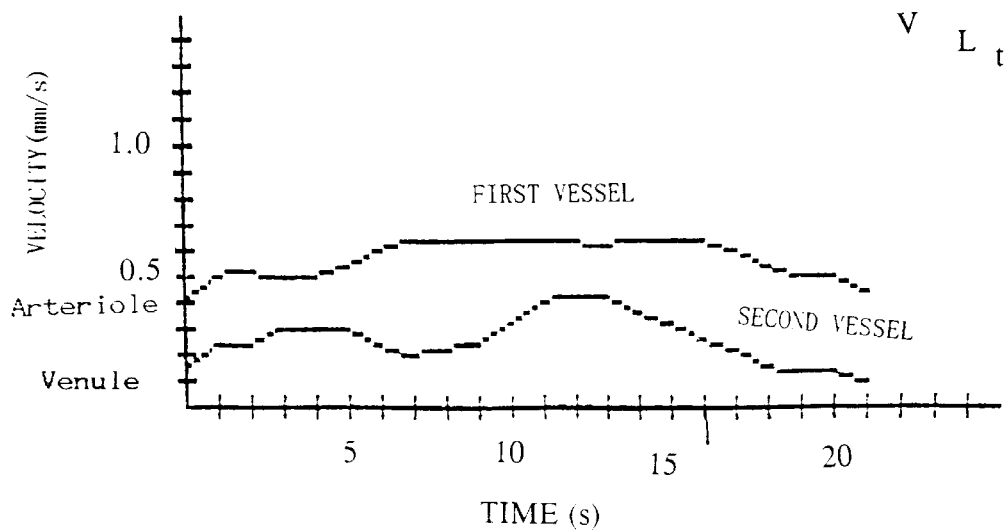

FIG. 6

MICROSCOPE SYSTEM FOR OBSERVATION AND DISPLAY OF MICROCIRCULATION AT MULTIPLE BODY AREAS

BACKGROUND OF THE INVENTION

The present invention relates to a microscope system for observation and display of microcirculation at multiple body areas, and more particularly to a measuring system in which a monitor is included to display microcirculatory image.

Most conventional microscope and photographic instruments use transmitted light to observe living specimens. Such conventional microscope and photographic instruments can not be directly used in clinical observation of different body areas because they have a short working distance and small depth of field, and the wavelength of light emitted from the light source does not match with the absorption spectrum of the observed object. Moreover, such conventional microscope and photographic instruments are not equipped with a photoelectric scanning and dynamic quantitative measuring system and therefore can not be used clinically to dynamically and quantitatively measure microcirculation at different body areas.

SUMMARY OF THE INVENTION

It is therefore a primary object of the present invention to provide a microscope system for observation and display of microcirculation at multiple body areas. The system includes an optical microscope and a display system. The optical microscope includes a set of object lenses with a long working distance and a high resolving power, as well as a double-optical-circuit light source that emits monochromatic lights matching with the absorption spectrum of red blood cells, thereby the monochromatic lights fall on the observed body and are reflected into the object lenses, so that red blood cells in capillaries and dynamic changes thereof can be detected. By analog-to-digital conversion, video signals are converted into digital image signals that can be processed by a computer. The digital image signals. are then stored in an image memory. The digital image signals can be stacked to graphic signals and converted into video images again via digital-analog conversion, so that microcirculatory images are displayed on the monitor.

BRIEF DESCRIPTION OF THE DRAWINGS

The main novel features of the present invention will become apparent from a careful consideration of the following detailed description of the preferred embodiments illustrated in the accompanying drawings, wherein:

FIG. 6 illustrates some testing data and curves indicating blood velocity in arterioles and venules obtained from the present invention.

DETAILED DESCRIPTION OF THE PREFERRED EMBODIMENTS

Figure 1:
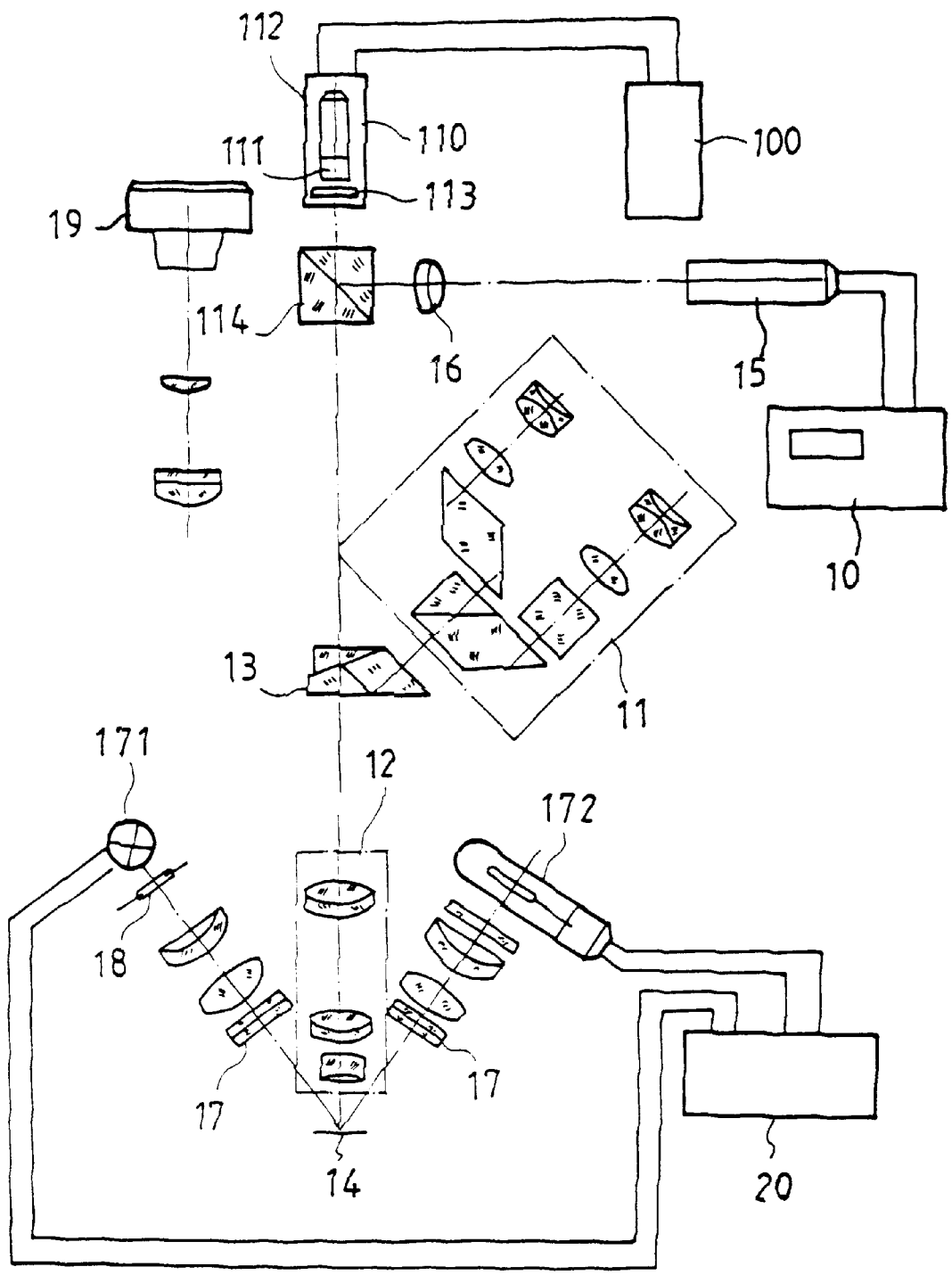
FIG. 1 is a schematic view showing the microscope included in the present invention.

According to physiological optics, when an object is observed under light from a light source, the light source must have an emission spectrum matching with an absorption spectrum of the observed object and the employed optical system must not produce any color difference in order to obtain clear, true and useful observation. Since the present invention relates to a microscopic system that is intended for observing microcirculation of blood in human body, it must be able to show clear and true colors to indicate red blood cells in capillaries. It is known that human red blood cells in capillaries have two major wavelengths of absorption spectrum, that is, 4150 Å and 5750 Å. In the present invention, a dual-optical-circuit monochromatic light source is included, and light beams from the light source are guided through multiple layers of medium film filters, so that their emission wavelengths fall between 4100 Å–4200 Å and 5700 Å–5800 Å, respectively. Red blood cells having absorbed monochromatic lights of these two wavelengths present a color darker than that they usually present On the other hand, a background of the observed red blood cells basically does not absorb lights of these two wavelengths and presents a color lighter than that of the red blood cells, producing a distinct contrast between the red blood cells and the background. In the microscopic system of the present invention, all optical elements provided in the optical circuit, including spectral prisms, are neutral or non-color difference elements, so that no color difference will be produced in the whole optical system of the present invention and the color of the red blood cells can be truly presented. In other words, the present invention enables clear and exact observation of red blood cells in capillaries and the dynamic changes thereof.

To allow the monochromatic lights to ideally penetrate skin and be fully absorbed by the red blood cells, a layer of liquid is applied on outer surface of the observed object. The observed object has a refraction coefficient matching with that of a first lens in the set of object lenses of the microscope. When the surface of the observed object and the applied liquid form an integral unit having a smooth surface, it enables large reduction of diffuse reflection and increase of transmission coefficient of the observed object surface.

To enable observations of dynamic changes in microcirculation at different human body areas, an optical microscope must have long working distance and high resolving power. In the present invention, object lenses are designed to have a focal length (F) of 32 mm that is longer than that of general object lenses having the same power. This allows the microscope of the present invention to have a working distance of 38 mm that is more than 10 mm longer than that of general microscopes having the same power and numerical aperture. In the following equation:

$$b = 0.61 \, \lambda/NA$$

wherein,
b=resolving power of the microscope;
λ=wavelength of light source; and
NA=numerical aperture of the microscope;
the resolving power of the microscope can be increased either by increasing the value of NA or using a light source having shorter wavelength. The microscope used in the present invention has object lenses that have a numerical aperture larger than that of similar object lenses by 0.01. The wavelength of light source used in the present invention is between 4100 Å and 4200 Å which is much shorter when compared with the light source used in other instruments, such as a halogen lamp that has a wavelength (λ) of 6000 Å. These conditions enable an increased resolving power of the microscope of the present invention.

In order to enable electronic flash instantaneous photography while observing the object through the microscope, the present invention includes a switch type microelectronic flash light provided in one of the two monochromatic light sources from the dual-optical-circuit and a switch type camera provided in the optical circuit of the optical microscope. Continuous winding of film is possible on the camera and therefore photos showing dynamic changes in the observed object can be taken. With the electronic flash instantaneous photography, each photo is taken at a shutter speed of 1/600 sec.

The microscope of the present invention includes a scotopic detection and video display system composed of a scotopic detector and a high-resolving-power video display. The scotopic detector has a receiver composed of coupled scotopic tube and pick-up tube. With the scotopic detector, photochronography is possible to take continuous pictures of red blood cells because the scotopic detector is highly sensitive to light reflected from red blood cells even at a very low light level.

The microscope system of the present invention can be widely clinically employed in medical department, surgical department, pediatrics department, gynecology department, brain system department, orthopedics department, department of traditional Chinese medicine, ophthalmology department, neurology department, tumors department, pathology department, physiotherapy department, ear-nose-throat department, acupuncture & moxibustion department, etc. to allow correct diagnosis, medication instruction, and emergent treatment at early stage. When the microscope system of the present invention is used to observe a patient, no surgical operation is needed. No pain or any side effect will be caused. And, the microscope system is of public hazard free. Light beams emitted from the light source in the present invention can directly penetrate into the patient's skin to clearly and truly display different conditions in the microcirculation of human body, such as angioma, cramp, dilatation, twist, winding, blood cell aggregation, and blood velocity in capillaries, so that microcirculation at multiple areas in human body can be continuously observed and quantitatively measured. The microscope system of the present invention is particularly helpful in early diagnosis, medication instruction, and emergent treatment of cardio-vascular diseases, cerebral apoplexy, necrosis of distal end of limbs caused by diabetes, angiitis, etc.

Please now refer to FIG. 1 that schematically illustrates the structure of an optical microscope according to the present invention. The microscope includes a high-eye-point, big visual field, flat field eyepiece 11, a set of long working distance object lenses 12, a first neutral spectral prism 13, a cathode-ray tube 15, an image formation lens 16, dual-optical-circuit monochromatic light sources 17, a high color temperature bromine-tungsten lamp 171, a high-pressure mercury-vapor lamp 172, a microelectronic flash light 18, a camera 19 that can be switched to the optical circuit, a scan, track and auto digits display system 10, a scotopic detector 110, a scotopic tube 111, a pick-up tube 112, an optical index plate 113, and a second neutral spectral prism 114.

Lights emitted from the high-color-temperature bromine-tungsten lamp 171 and the high-pressure mercury-vapor lamp 172 respectively are transmitted through optical systems having correspondingly arranged multiple layers of medium film filters to produce monochromatic lights having wavelengths of 5800 Å and 4100 Å, respectively. These two beams of monochromatic light, powered by power source 20, fall on an observed object 14 simultaneously. The light beams are reflected from the observed object 14 to pass the long working distance object lenses 12 and the first and the second spectral prisms 13, 114, forming an image on a picture plate of the scotopic detector 110. The image on the picture plate is sent to a video display system 100 and is displayed on a screen of the video display system to clearly and truly show capillaries in the observed object and blood flows in the capillaries. Meanwhile, scanning light-spots on a fluorescent screen of the cathode-ray tube 15 are reduced by the image formation lens 16 before they pass the second neutral spectral prism 114, and also form an image on the picture plate of the scotopic detector 110. The light-spot scanned image on the picture plate is also sent to the video display system 100 and is shown on the screen. The scan, track and auto digit display system 10 regulates the velocity, direction and angle of the light-spot scanning, so that the scan and track is proceeded at a speed and in a direction the same as that of the blood flow. Whether the scan and track is proceeded at a speed and in a direction the same as that of the blood flow can be detected and determined by observing the clear image on the video display system 100. The light-spot scanning velocity indicated on a nixie tube of the scan, track and auto digit display system 10 at that time is the blood flow speed. Since the optical index plate 113 has scales thereon and the scales are also clearly shown in the video display system 100, inner diameters and lengths of capillaries can be directly measured on the display system 100.

When an instantaneous photographing is desired, the electronic flash light 18 and the camera 19 may be switched to the optical circuit. With the microelectronic flash light 18 serving as an auxiliary light source, instantaneous photos of capillaries and flowing blood cells can be taken while they are observed under the microscope.

In addition to the microcirculation of blood in human body, the microscopic system of the present invention may also be used to clinically observe the microcirculation of blood of other animals. Microcirculation of other systems, such as lymph, may also be clinically observed with the present invention.

Figure 2:
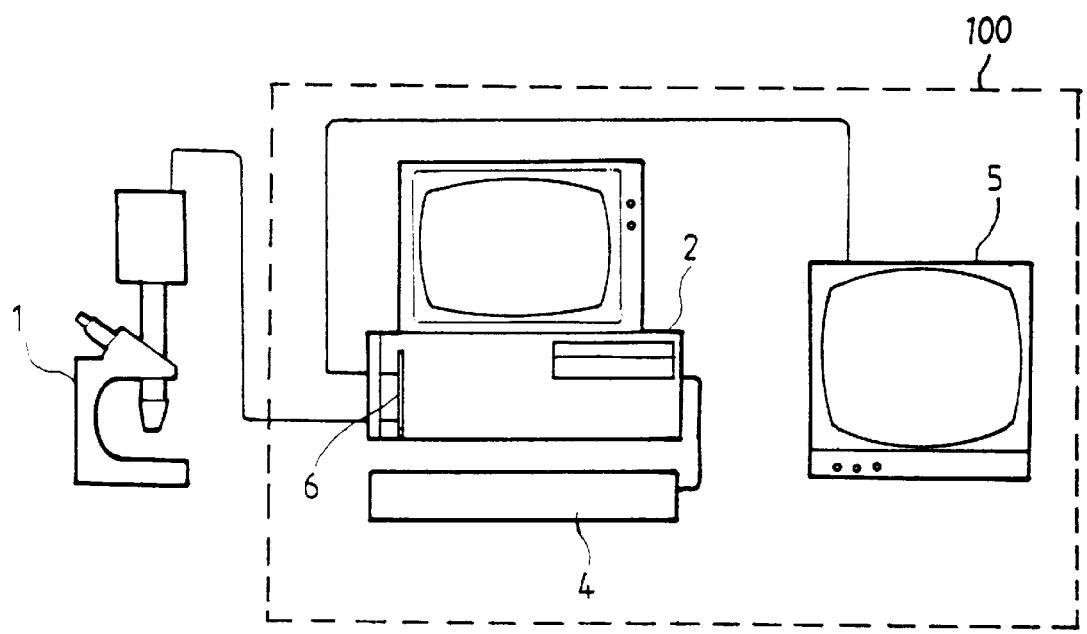
FIG. 2 is a schematic view showing the display system included in the present invention.

Please now refer to FIG. 2 that schematically illustrates the display system of the present invention. As shown, the display system mainly includes a computer mainframe 2, a microcomputer 4, and a monitor 5. Images showing the circulation of blood in arterioles, capillaries, and venules of human blood circulation system are obtained via a microscope 1. After conversion by an analog-to-digital converter in the mainframe 2 and stacking of the images with digits in an image card 6 by the microcomputer 4, the images of circulation are directly displayed on the monitor 5 to enable measuring of microcirculation.

Figure 3:
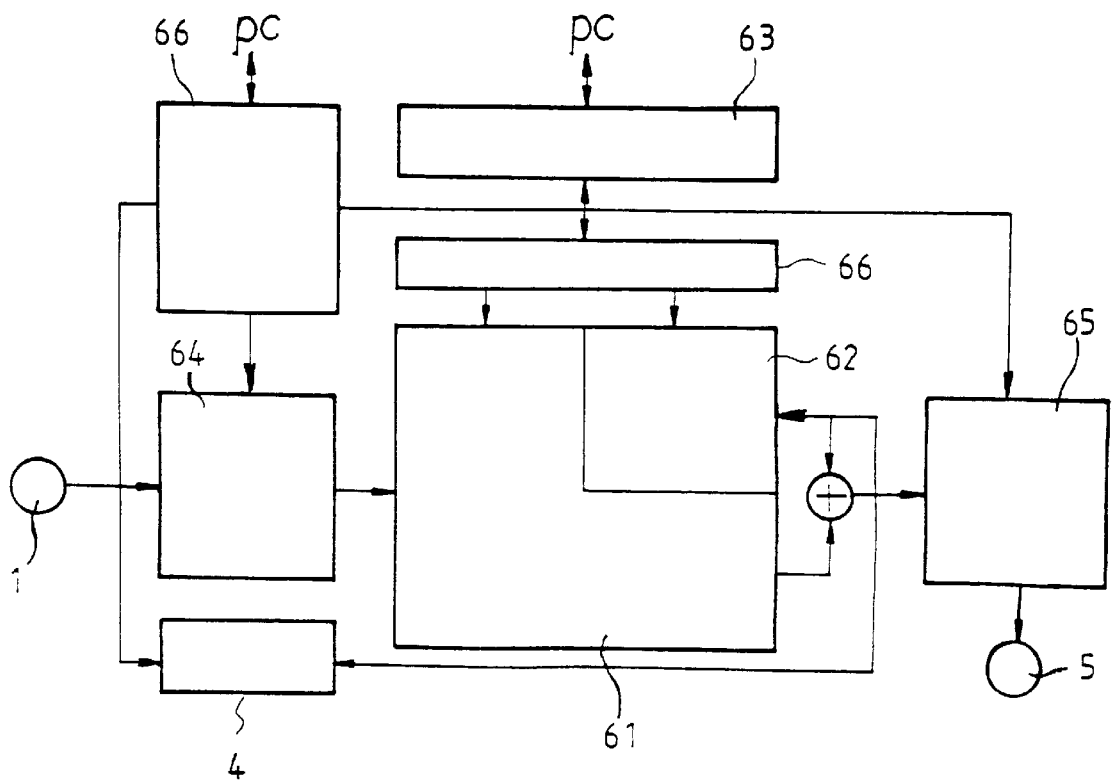
FIG. 3 is a block diagram of an image card according to the present invention.

Please refer to FIG. 3 that is a block diagram of the circuit of the image card 6 according to the present invention. As shown, the circuit of the image card 6 mainly includes an image memory 61, a graph memory 62, a buffer memory 63, an analog-to-digital converter 64, a digital-analog converter 65, and control circuits 66. Wherein, the image memory 61 is a storage for storing image data and has four pages for each storing one image. The graph memory 62 is similar to the image memory 61 but is used to store graphs. The analog-to-digital converter 64 is used to collect image signals sent from the mainframe 2 and to convert video simulated signals into digital signals. The images are then stored in the image memory 61 in the sequence of collection. The digital-analog converter 65 stacks digits retrieved from the image memory 61 and the graph memory 62 and converts them into video simulated signals. The control circuits 66 control operations of the above-described elements of the image card 6.

With the above arrangements, the microscope 1 takes images of microcirculation of blood, and the images are then converted by the analog-to-digital converter 64 from video simulated signals into digital image signals that can be processed by the computer and the converted digital image signals are stored in the image memory 61. The digital image signals are then stacked to digital graph signals in the graph memory 62. The resultant signals are output to the digital-analog converter 65 to be converted into video simulated signals that can be used by the monitor 5 and are sent to the monitor 5, so that images of microcirculation with stacked graphs are displayed on the monitor 5.

Figure 4:
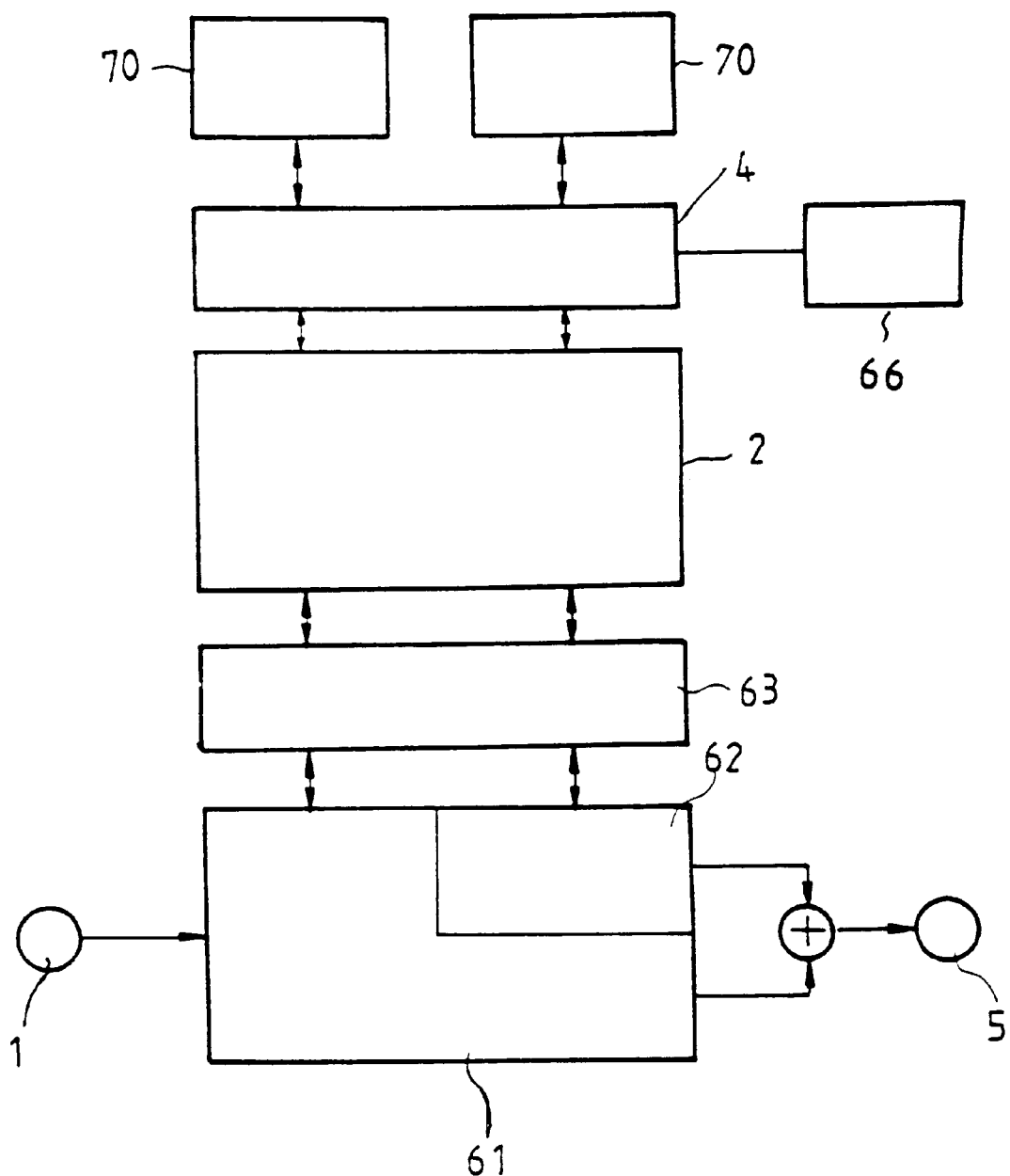
FIG. 4 is allow chart of the operation of the image card of FIG. 3.
Figure 5:
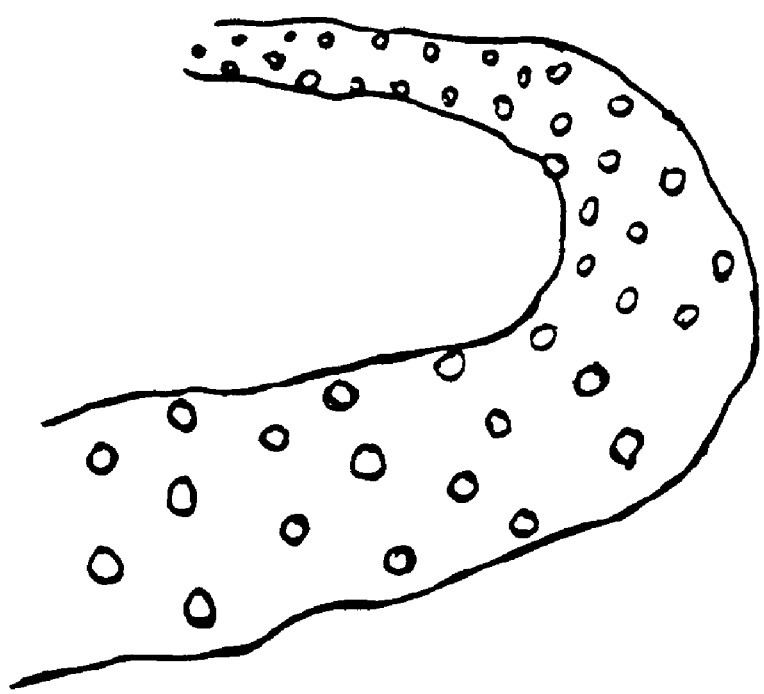
FIG. 5 schematically shows a microcirculatory image displayed by the present invention.

FIG. 4 is an operation flow chart of the image card 6. As shown, the microscope 1 is connected to the image memory 61 so that video simulated signals can be converted into digital signals. The image memory 61 is connected to the computer mainframe 2 via a bidirectional close circuit of the buffer memory 63, so that a CPU in the mainframe 2 may proceed various processes in association with stacking circuits 70 and control circuits 66 according to instructions of an operator. The processed image data are sent back to the image memory 61 and can be displayed on the monitor 5 for observation. FIG. 5 is an example of the microcirculation image obtained from the present invention. The flowing of blood is clearly and completely shown in the image. FIG. 6 illustrates correlation test data of the present invention as well as curves showing blood velocity in arteries and veins. A tester may observe the condition of microcirculation not only from the images but from the displayed test data and curves.

In brief, the present invention employs image and graph memories as well as microscope and monitor to display measuring images of microcirculation on the monitor. The present invention is novel in design and practical for use.

What is claimed is:

1. A microscope system for observation and display of microcirculation of blood at multiple body areas, comprising:

a monochromatic light generator which comprises a high-pressure mercury-vapor lamp, a high-temperature tungsten lamp, and a set of multiple film filters for emitting lights of wavelengths of 4100 Å and 5800 Å respectively, said tungsten lamp being equipped with an electronic flash to be switched to take an instantaneous photograph with a camera;

a microscope, comprising a set of eye lenses with a long working distance, a high resolving power a high eyepoint, a set of object lenses having a focus length of 32 mm, and a scotopic detector for accepting monochromatic light emitted from a dual-optical-circuit source, said scotopic detector comprising a scotopic tube and a pick-up tube, said focus length allowing said microscope to have a working distance of 38 mm;

a display system comprising an analog-to-digital converter, a microcomputer and a monitor, said display system converting images of microcirculation of blood viewed under said microscope into digital signals, stacking said digital signals to graph signals stored in an image card, converting said stacked signals into analog signals, and sending said analog signals to the monitor to display said images of microcirculation of blood.

* * * * *